United States Patent [19]

Bott et al.

[11] Patent Number: 5,514,762

[45] Date of Patent: May 7, 1996

[54] COPOLYMERIZABLE OXIME ETHERS AND COPOLYMERS CONTAINING THEM

[75] Inventors: Kaspar Bott, Mannheim; Gerhard Bauer, Weinheim; Karl Haeberle, Speyer, all of Germany

[73] Assignee: BASF Aktiengesellschaft, Ludwigshafen, Germany

[21] Appl. No.: 325,091

[22] Filed: Oct. 17, 1994

Related U.S. Application Data

[62] Division of Ser. No. 202,215, Feb. 25, 1994.

[30] Foreign Application Priority Data

Mar. 22, 1993 [DE] Germany .................... 43 09 193.8

[51] Int. Cl.⁶ .................................................. C08F 226/02
[52] U.S. Cl. ............................................. 526/301; 526/311
[58] Field of Search ................................... 526/301, 311; 525/328.2

[56] References Cited

FOREIGN PATENT DOCUMENTS 58-093048  6/1983  Japan .

Primary Examiner—Mark Nagumo
Attorney, Agent, or Firm—Oblon, Spivak, McClelland, Maier & Neustadt

[57]  ABSTRACT

Copolymerizable oxime ethers of the general formula

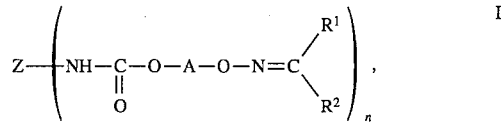

where A is a divalent linking member, $R^1$ and $R^2$ independently of one another are each $C_1$-$C_{10}$-alkyl, $C_1$-$C_{10}$-alkoxy, $C_5$-$C_{10}$-cycloalkyl or $C_5$-$C_{10}$-aryl, each of which may furthermore contain 1–3 nonadjacent nitrogen, oxygen or sulfur atoms as heteroatoms in the carbon chain or in the carbon ring and may be substituted by from one to three $C_1$-$C_4$-alkyl or $C_1$-$C_4$-alkoxy groups, $R^1$ or $R^2$ may be hydrogen or $R^1$ and $R^2$ together form a bridge of 3 to 14 carbon atoms, where some of the carbon atoms may furthermore be part of an aromatic ring, Z is an n-valent organic radical which contains a copolymerizable ethylenically unsaturated group and n is an integer of from 1 to 3.

2 Claims, No Drawings

COPOLYMERIZABLE OXIME ETHERS AND COPOLYMERS CONTAINING THEM

This is a division, of application Ser. No. 08/202,215 filed on Feb. 25, 1994.

The present invention relates to copolymerizable oxime ethers of the general formula

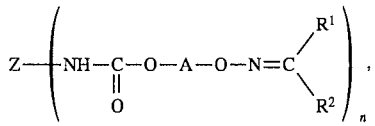

where A is a divalent linking member, $R^1$ and $R^2$ independently of one another are each $C_1$-$C_{10}$-alkyl, $C_1$-$C_{10}$-alkoxy, $C_5$-$C_{10}$-cycloalkyl or $C_5$-$C_{10}$-aryl, each of which may furthermore contain 1–3 nonadjacent nitrogen, oxygen or sulfur atoms as heteroatoms in the carbon chain or in the carbon ring and may be substituted by from one to three $C_1$-$C_4$-alkyl or $C_1$-$C_4$-alkoxy groups, $R^1$ or $R^2$ may be hydrogen or $R^1$ and $R^2$ together form a bridge of 3 to 14 carbon atoms, where some of the carbon atoms may furthermore be part of an aromatic ring, Z is an n-valent organic radical which contains a copolymerizable ethylenically unsaturated group and n is an integer of from 1 to 3.

The present invention furthermore relates to copolymers which contain the oxime ethers, and to a process for the preparation of the oxime ethers.

Copolymers which are used in coating materials for example in lacquers or varnishes, or adhesives are often crosslinkable copolymers. As a result of crosslinking, it is possible to obtain, for example, protective coatings or adhesive coatings having good elastic properties, high cohesion and good resistance to chemicals and to solvents.

The copolymers are crosslinked in general by adding a crosslinking agent which reacts with functional groups in the copolymer. Examples of possible crosslinking agents are polyisocyanates, which react with hydroxyl or amino groups.

DE-A-35 21 618 discloses corresponding aqueous adhesive formulations in which polyisocyanates dispersed in water are added, as crosslinking agents, to aqueous dispersions of copolymers obtained by free radical polymerization. Similar adhesive formulations are also described in US-A-43 96 738 and DE-A-31 12 117.

However, the disadvantage of these aqueous formulations is the poor shelf life. The polyisocyanate may therefore be dispersed in water and mixed with the copolymer only shortly before it is used as the crosslinking agent.

A longer shelf life can be achieved by reacting the isocyanate groups with blocking agents, for example oximes, caprolactam, phenols or dialkyl maleates. The blocked polyisocyanates obtained undergo hydrolysis in aqueous dispersion only to a minor extent.

DE-A-38 07 555 relates to such an oxime-blocked diisocyanate which is dispersed in water and is suitable as an additive for polymers dispersed in water.

However, crosslinking reactions do not occur until after elimination of the blocking agent at above about 130° C.

Conventional aqueous adhesive formulations containing polyisocyanates as crosslinking agents therefore either do not have a sufficiently long shelf life and therefore can only be used as a 2-component system or crosslink only at high temperatures.

Aqueous dispersions which have a long shelf life and crosslink at room temperature after removal of the solvent are disclosed in EP-A-3516. These dispersions contain polyhydrazides which react with carbonyl-containing monomers polymerized in the copolymer.

Furthermore, EP-A-516 074 discloses dispersions which contain aminoxy crosslinking agents. German Patent Applications DE-A-41 21 946.5 and P 42 19 385.0 disclose, respectively, oxime-blocked polyisocyanates and copolymerizable oxime ethers as crosslinking agents. Crosslinking occurs in each case with carbonyl-containing copolymers.

It is in principle desirable to develop further dispersions having a long shelf life which crosslink at room temperature, in order to provide alternatives to polyhydrazide crosslinking.

It is an object of the present invention to provide crosslinkable copolymers which have a long shelf life in dispersion or solution, even in the presence of a crosslinking agent, and can be crosslinked at room temperature.

We have found that this object is achieved by the copolymerizable oxime ethers defined above and a process for the preparation of oxime ethers.

We have also found copolymers which contain the copolymerizable oxime ethers, and the use of the copolymers as coating materials or adhesive.

The copolymers which contain the copolymerizable oxime ethers exhibit good adhesion to a very wide range of substrates and crosslink in particular with compounds containing aldehyde or keto groups.

A in the general formula I is preferably a linear or branched hydrocarbon chain of 2 to 12, in particular 2 to 8, carbon atoms which may be interrupted by 1 to 3, in particular 1 or 2, nonadjacent sulfur or nitrogen atoms, preferably oxygen atoms, or a $C_5$-$C_{10}$-cycloalkylene or $C_5$-$C_{10}$-arylene ring. It is particularly preferably a linear or branched hydrocarbon chain of 2 to 8 carbon atoms.

$R^1$ and $R^2$ independently of one another are each preferably hydrogen, $C_1$-$C_6$-alkyl, $C_1$-$C_6$-alkoxy or $C_5$-$C_{10}$-aryl, in particular a phenyl ring. In the case of the hydrogen atom, only one of the two radicals $R^1$ and $R^2$ may be hydrogen. n is an integer from 1 to 3, preferably 1.

Z is an organic radical which contains a copolymerizable ethylenically unsaturated group.

Z as such may be a known monomer for free radical polymerization which, according to formula I, is substituted by a group

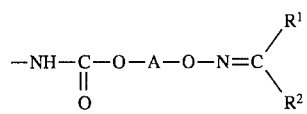

Examples of suitable radicals Z are vinyl aromatic radicals of up to 20 carbon atoms, (meth)acrylate radicals of the formula

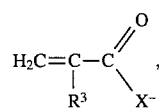

where $R^3$ is hydrogen or methyl and X is an organic linking member of, preferably, 1 to 20 carbon atoms, particularly preferably $C_1$-$C_{10}$-alkylene.

Other suitable radicals Z are ethylenically unsaturated groups having a urethane group, as are obtainable by reacting monomers reactive toward isocyanate with isocyanates, in particular diisocyanates.

Z is, particularly preferably, a (meth)acryloyl group of the formula

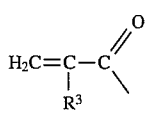
II

The copolymerizable oxime ethers of the formula I can be prepared by reacting an oxime ether alcohol of the formula

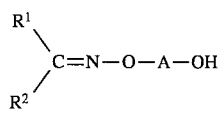
III with an isocyanate compound of the formula

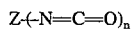
IV

The reaction can be carried out in a simple manner at, preferably, from 0 to 50° C., in particular from 0 to 20° C., by combining the starting compounds, preferably using a stoichiometric ratio of the oxime ether alcohol to the isocyanate groups. The reaction is preferably carried out in the presence of a solvent. Examples of solvents are aromatic or aliphatic hydrocarbons and chlorohydrocarbons. German Patent Application P 42 19 385.0 describes a process for the preparation of copolymerizable oxime ethers by reacting an oxime ether alcohol with (meth)acryloyl chloride or (meth)acrylic anhydride in the presence of a base. This process produces a considerable amount of salt, which is avoided in the novel process described above.

The oxime ether alcohols of the formula III as starting compounds for the reaction are obtainable by known processes, for example by reacting oximes with alkylene oxides, such as ethylene oxide, propylene oxide, etc., or with haloalcohols in the presence of a base.

The isocyanate compounds IV are monomers capable of undergoing free radical polymerization, i.e., compounds which have a copolymerizable ethylenically unsaturated group and contain at least one isocyanate group.

Examples of suitable isocyanate compounds are (meth)acryloyl isocyanate and $C_1$-$C_{10}$-alkyl (meth)acrylates which are substituted in the alkyl radical by at least one, preferably one, isocyanate group. e.g., 2-isocyanatoethyl (meth)acrylate or m- or p-isopropenyl-$\alpha,\alpha'$-dimethylbenzyl isocyanate.

The isocyanate compounds IV can also be prepared in a simple manner by first reacting polyisocyanates, in particular diisocyanates, with ethylenically unsaturated compounds so that at least one free isocyanate group remains. Suitable ethylenically unsaturated compounds are those which have at least one group reactive toward isocyanate, for example a primary or secondary amino group or, preferably, a hydroxyl group. These may be reacted in a known manner with a polyisocyanate, urea or urethane formation taking place. Ethylenically unsaturated compounds having a hydroxyl group, for example hydroxy-$C_2$-$C_{10}$-alkyl (meth)acrylates, are preferably reacted with polyisocyanates, in particular diisocyanates. Examples of suitable diisocyanates are those of the general formula $X(NCO)_2$, where X is an aliphatic hydrocarbon radical of 4 to 12 carbon atoms, a cycloaliphatic hydrocarbon radical of 6 to 15 carbon atoms or an aromatic or alkaromatic hydrocarbon radical of 6 to 15 carbon atoms. Examples are butane 1,4-diisocyanate, hexane 1,6-diisocyanate, 2,2,4- and 2,4,4-trimethylhexamethylene diisocyanate, cyclohexane diisocyanate, methylcyclohexane diisocyanate, isophorone diisocyanate, 4,4'-diisocyanatodiphenylmethane, 4,4'-diisocyanatodicyclohexylmethane and 2,4- and 2,6-toluylene diisocyanate.

The copolymerizable oxime ethers (also referred to below as monomers a)) can be copolymerized with ethylenically unsaturated monomers by conventional methods of free radical polymerization.

For sufficient crosslinkability and good adhesion of the resulting copolymers, the content of polymerized oxime ethers a) should be at least 0.01% by weight. A content of more than 30% by weight is in general unnecessary.

The content of polymerized oxime ethers in the copolymer is preferably from 0.1 to 10, particularly preferably from 0.1 to 5, % by weight.

The copolymers contain, as main monomers b), 30–99.99, preferably 70–99.9, particularly preferably 85–99.9, % by weight of a monomer selected from the group consisting of $C_1$-$C_{20}$-alkyl (meth)acrylates, vinyl esters of carboxylic acids of up to 20 carbon atoms, vinyl aromatics of up to 20 carbon atoms, ethylenically unsaturated nitriles, vinyl halides and nonaromatic hydrocarbons having at least 2 conjugated double bonds.

Examples of main monomers are alkyl (meth)acrylates having a $C_1$-$C_{10}$-alkyl radical, such as methyl methacrylate, methyl acrylate, n-butyl acrylate, ethyl acrylate and 2-ethylhexyl acrylate.

Mixtures of the alkyl (meth)acrylates are also particularly suitable.

Vinyl esters of carboxylic acids of 1 to 20 carbon atoms are, for example, vinyl laurate, stearate, propionate and acetate.

Suitable vinylaromatic compounds are vinyltoluene, $\alpha$- and p-methylstyrene, $\alpha$-butylstyrene, 4-n-butylstyrene, 4-n-decylstyrene and preferably styrene. Examples of nitriles are acrylonitrile and methacrylonitrile.

The vinyl halides are ethylenically unsaturated compounds substituted by chlorine, fluorine or bromine, preferably vinyl chloride and vinylidene chloride.

Examples of nonaromatic hydrocarbons having 2 to 8 carbon atoms and at least two olefinic double bonds are butadiene, isoprene and chloroprene.

The main monomers are also preferably used as a mixture.

The copolymers may furthermore contain monomers having at least one aldehyde or keto group (monomers c)).

These are preferably monomers having one or two aldehyde or keto groups or one aldehyde and one keto group and an olefinic double bond capable of undergoing free radical polymerization.

For example, acrolein, methacrolein, vinyl alkyl ketones where the alkyl radical is of 1 to 20, preferably 1 to 10, carbon atoms, formylstyrene, alkyl (meth)acrylates where the alkyl radical contains one or two keto or aldehyde groups or one aldehyde and one keto group and is preferably of, in total, 3 to 10 carbon atoms, for example (meth)acryloyloxyalkylpropanals, as described in DE-A-27 22 097, are suitable. N-Oxoalkyl(meth)acrylamides as disclosed in, for example, US-A-4 226 007, DE-A-20 61 213 or DE-A-22 07 209 are also suitable.

Acetoacetyl (meth)acrylate, acetoacetoxyethyl (meth)acrylate and in particular diacetoneacrylamide are particularly preferred.

The content of these monomers is in general from 0 to 30, in particular from 0 to 10, particularly preferably from 0 to 5, % by weight.

The copolymer may be self-crosslinkable or externally crosslinkable. In the case of self-crosslinkability, it contains both copolymerizable oxime ethers and, preferably, monomers having at least one keto or aldehyde group. The crosslinking of the copolymer then takes place without the addition of a crosslinking agent, by reaction of the oxime group with the keto or aldehyde group in the same copolymer.

In this case, the copolymer should preferably contain at least 0.1% by weight of the monomer having at least one keto or aldehyde group c). The maximum possible amount of main monomer is then reduced by 0.1% by weight. In order to obtain good adhesion, it is not essential for monomers c) to be present.

Examples of further monomers d) which differ from the monomers a) to c) and may be present in the copolymer are esters of acrylic and methacrylic acid with alcohols of 1 to 20 carbon atoms which contain at least one further heteroatom in addition to the oxygen atom in the alcohol group and/or which contain an aliphatic or aromatic ring, such as 2-ethoxyethyl acrylate, 2-butoxyethyl (meth)acrylate, dimethylaminoethyl (meth)acrylate, diethylaminoethyl (meth)acrylate, aryl, alkaryl or cycloalkyl (meth)acrylates, such as cyclohexyl (meth)acrylate, phenylethyl (meth)acrylate or phenylpropyl (meth)acrylate, or esters of acrylic acid with heterocyclic alcohols, such as furfuryl (meth)acrylate.

Further monomers, such as (meth)acrylamide and its derivatives substituted by $C_1$-$C_4$-alkyl at the nitrogen, are also suitable.

Monomers containing hydroxyl functional groups, for example $C_1$-$C_{15}$-alkyl (meth)acrylates which are substituted by one or two hydroxyl groups, are also important. Particularly important comonomers containing hydroxyl functional groups are $C_2$-$C_8$-hydroxyalkyl (meth)acrylates, such as n-hydroxyethyl, n-hydroxypropyl or n-hydroxylbutyl (meth)acrylate.

The presence of comonomers having salt-forming groups is preferable for the preparation of self-dispersible copolymers which are suitable, for example, for aqueous secondary dispersions. Monomers having salt-forming groups are, in particular, itaconic acid, acrylic acid and methacrylic acid.

The amount of the further comonomers in the copolymer may be from 0 to 50, preferably from 0 to 20, very particularly preferably from 0 to 10, % by weight.

The copolymer a) is prepared by free radical polymerization. Suitable polymerization methods, such as mass, solution, suspension or emulsion polymerization, are known to the skilled worker.

The copolymer is preferably prepared by solution polymerization with subsequent dispersing in water or particularly preferably by emulsion polymerization.

In the emulsion polymerization, the comonomers can be polymerized in a conventional manner in the presence of a water-soluble initiator and of an emulsifier at preferably from 30 to 95° C.

Examples of suitable initiators are sodium persulfate, potassium persulfate, ammonium persulfate, tert-butyl hydroperoxides, water-soluble azo compounds or redox initiators.

The emulsifiers used are, for example, alkali metal salts of relatively long-chain fatty acids, alkylsulfates, alkylsulfonates, alkylated arylsulfonates or alkylated diphenyl ether sulfonates. Other suitable emulsifiers are reaction products of alkylene oxides, in particular ethylene oxide or propylene oxide, with fatty alcohols, fatty acids or phenol, or alkylphenols.

In the case of aqueous secondary dispersions, the copolymer is first prepared by solution polymerization in an organic solvent and then dispersed in water with the addition of salt formers, for example of ammonia to carboxyl-containing copolymers, and without the use of an emulsifier or dispersant. The organic solvent can be distilled off. The preparation of aqueous secondary dispersions is known to the skilled worker and is described in, for example, DE-A-37 20 860.

Regulators may be used in the polymerization in order to adjust the molecular weight. For example, -SH-containing compounds, such as mercaptoethanol, mercaptopropanol, thiophenol, thioglycerol, ethyl thioglycolate, methyl thioglycolate and tert-dodecyl mercaptan, are suitable.

The type and amount of the comonomers are advantageously chosen so that the resulting copolymer has a glass transition temperature of, preferably, from −60 to 140° C., particularly preferably from −30 to +80° C. for example in the case of lacquers, very particularly preferably, especially for use as an adhesive, from −30 to +20° C. The glass transition temperature of the copolymer can be determined by conventional methods, such as differential thermal analysis or differential scanning calorimetry (cf. for example ASTM 3418/82, i.e., midpoint temperature).

Where the copolymer is not self-crosslinking, i.e., contains no monomers c), a suitable crosslinking agent may be added to the copolymer to effect crosslinking. The crosslinking agent is usually a compound which contains at least two keto or aldehyde groups or at least one keto–and one aldehyde group.

Such compounds are, for example, succinaldehyde, glutaraldehyde and terephthalaldehyde.

Other suitable crosslinking agents are in particular copolymers obtained by free radical copolymerization, which are also referred to below as polymeric crosslinking agents and contain abovementioned monomers c) as polymerized units.

For example, polymeric crosslinking agents which are composed of 30–99.9, preferably 70–99.9, % by weight of the monomers b), 0.1–30, preferably 0.1–10, % by weight of the monomers c) and 0–50, preferably 0–20, % by weight of the monomers d) are suitable. The statements made above concerning the above copolymers apply to the type of monomers, the glass transition temperature and the preparation.

The novel copolymers may furthermore crosslink with hydroxyl-containing compounds, in particular hydroxyl-containing copolymers.

The crosslinking agent, if required, is preferably added to the solution or dispersion of the copolymers.

However, it is also possible to combine the copolymer and the crosslinking agent only when they are used, for example in the coating of surfaces. For this purpose, for example, the crosslinking agent could first be applied to the surface as a primer and coating could then be effected with the dispersion or solution of the copolymers.

The solution or dispersion of the novel copolymers is suitable, for example, for use as coating materials, for example as varnishes or lacquers for protective or decorative purposes, for various substrates having plastic, wood or metal surfaces or, for example, for textiles, nonwovens, leather or paper. They are also useful for applications in building chemistry, for example as adhesives, sealing compounds, binders or the like.

The dispersions or solutions may also contain conventional assistants or additives, depending on the intended use. These include, for example, fillers, such as quartz powder, quartz sand, finely divided silica, barite, calcium carbonate, chalk, dolomite or talc, which are often used together with suitable wetting agents, for example polyphosphates, such as sodium hexametaphosphate, naphthalenesulfonic acid or ammonium or sodium polyacrylates, the wetting agents being added in general in amounts of from 0.2 to 0.6% by weight, based on the filler.

Fungicides for preservation may also be added. These are used in general in amounts of from 0.02 to 1% by weight, based on the dispersions or solutions. Examples of suitable fungicides are phenol derivatives or cresol derivatives or organotin compounds.

When used for coating, then all dispersions or solutions may contain additives typical for coatings, such as film forming assistants, pigments, flatting agents, thickeners, pigment dispersants, antifilms, etc. and natural or synthetic resins, e.g., alkyd resins or polyurethane resins.

The dispersions or solutions are also particularly suitable as sealing or adhesive formulations, in particular as laminating adhesives for the production of laminated films and high-gloss films. As such, they may contain, in addition to the abovementioned additives, also specific assistants and additives conventionally used in adhesives technology. These include, for example, thickeners, plasticizers or tackifiers, for example natural resins or modified resins, such as rosin esters, or synthetic resins, such as phthalate resins.

The dispersions or solutions of the self crosslinking or externally crosslinking copolymers which also contain a crosslinking agent have a long shelf life. Crosslinking occurs at as low as room temperature with volatilization of the solvent. The crosslinkability and the good adhesive properties of the copolymers are not adversely affected by the presence of metal salts.

The coatings or adhesive bonds produced using these dispersions or solutions have good resistance to chemicals and to solvents and good internal strength (cohesion). Preparation of copolymerizable oxime ethers V1–V5 (3-Methacrylamidocarbonyloxypropyl)-acetone oxime ether (V1)

A solution of 55.5 g (0.50 mol) of methacryloyl isocyanate in 50 ml of dichloromethane was added dropwise to a mixture of 65.5 g (0.50 mol) of 0-(3-hydroxypropyl)acetone oxime and 100 ml of dichloromethane in the course of 30 minutes at 10° C. The reaction was continued for 2 hours at 10° C. and the solvent was evaporated off at room temperature under reduced pressure. The distillation residue consisted of 121 g (yield 100%) of crystalline product which, after recrystallization from methyl tertbutyl ether (at −25° C.), melted at 51°–53° C.

Elemental analysis:
Calc. C 54.53 H 7.49 O 26.41 N 11.56
C 54.7 H 7.6 O 26.6 N 11.8

Correct elemental analyses and H-NMR spectra were obtainable for all copolymerizable oxime ethers in Table 1.

The preparation of the copolymerizable oxime ethers V2 to V5 was carried out similarly to V1. Table 1 shows the starting materials and products with their structural formulae.

TABLE 1

Copolymerizable oxime ethers V1 to V5

| Example | Starting materials | Polymerizable oxime ethers, melting point |
|---|---|---|
| V1 | $H_2C=C(CH_3)-C(=O)-N=C=O$ ; $(H_3C)_2C=N-O-(CH_2)_3-OH$ | $H_2C=C(CH_3)-C(=O)-NH-C(=O)-O-(CH_2)_3-O-N=C(CH_3)_2$ ; 51–53° C. |
| V2 | $H_2C=C(CH_3)-C(=O)-N=C=O$ ; $(H_3C)_2C=N-O-(CH_2)_2-OH$ | $H_2C=C(CH_3)-C(=O)-NH-C(=O)-O-(CH_2)_2-O-N=C(CH_3)_2$ ; 83–85° C. |
| V3 | $H_2C=C(CH_3)-C(=O)-N=C=O$ ; $(H_3C)_2C=N-O-CH_2-CH(CH_3)-OH$ | $H_2C=C(CH_3)-C(=O)-NH-C(=O)-O-CH(CH_3)-CH_2-O-N=C(CH_3)_2$ ; 71–73° C. |

TABLE 1-continued

Copolymerizable oxime ethers V1 to V5

| Example | Starting materials | Polymerizable oxime ethers, melting point |
|---------|-------------------|-------------------------------------------|
| V4 | $H_2C=C(CH_3)-C(O)-N=C=O$ <br> $(H_3C)(H_5C_2O)C=N-O-(CH_2)_2-OH$ | $(H_3C)(H_5C_2O)C=N-O-(CH_2)_2-O-C(O)-NH-C(O)-C(CH_3)=CH_2$ <br> 66–68° C. |
| V5 | $H_2C=C(CH_3)-C(O)-N=C=O$ <br> $(Ph)(H_3C)C=N-O-(CH_2)_2-OH$ | $(Ph)(H_3C)C=N-O-(CH_2)_2-O-C(O)-NH-C(O)-C(CH_3)=CH_2$ <br> 57–60° C. |

Preparation of the dispersions D1 to D15

Dispersion D1

200 g of demineralized water, 37 g of feed 1 (see below) and 20 g of feed 2 were initially taken in a reaction vessel having a stirrer and two feed vessels (feed 1 and feed 2) and were heated to 85° C. After 15 minutes, feed 1 was added uniformly to the reaction vessel in the course of 2 hours, and feed 2 uniformly in the course of 2.5 hours. After the final addition of the initiator (feed 2), the dispersion was stirred for a further hour at 85° C.

Feed 1: (this feed was stirred during the polymerization)
107.5 g of demineralized water
400 g of ethyl acrylate
90 g of methyl methacrylate
50 g of 20% strength by weight aqueous diacetone acrylamide solution
50 g of 20% strength by weight solution of the sodium salt of p-dodecyldiphenylether disulfonate in water (emulsifier)
50 g of 20% strength by weight solution of the reaction product of p-isononylphenol with about 50 mol of ethylene oxide in water (emulsifier)

Feed 2:
100 g of demineralized water
3 g of sodium persulfate

The dispersions D2 to D15 were prepared in a similar manner. The composition of the particular copolymers is shown in Table 2.

Crosslinkability (test based on swelling behavior and determination of the extractables)

10 g of each dispersion were converted into a film, and the films were dried for 1 week at room temperature. Thereafter, the swelling behavior in tetrahydrofuran was investigated as a measure of the degree of crosslinking of these films, by storing about 1 g of the samples in the form of a film in tetrahydrofuran for 2 days and measuring the solvent absorption in % (results in Table 6).

In the case of crosslinked polymers, swelling occurs as a result of the absorption of solvent. The swelling decreases with increasing degree of crosslinking, since less solvent can be absorbed by densely crosslinked polymers. Polymers which are not crosslinked or are slightly crosslinked are to a considerable extent dissolved by solvents or swell to an excessive extent when a small number of crosslinking sites are present.

The extractables were determined by reweighing at room temperature after drying in a drying oven at 80° C. for 4 hours.

TABLE 2

Dispersions D1–D15, composition and crosslinking behavior

| Dispersion | Composition of the copolymers in % by weight | Swelling behavior Increase in % by weight | Extractables in % by weight |
|------------|----------------------------------------------|-------------------------------------------|------------------------------|
| D1 | 80 EA/18 MHA/2 DAA | —* | —* |
| D2 | 80 nBA/18 MMA/2 DAA | —* | —* |
| D3 | 78 EA/18 MMA/2 HEA/2 DAA | —* | —* |
| D4 | 78 EA/18 MMA/2 DAA/2 V1 | 720 | 7 |
| D5 | 78 nBA/18 MMA/2 DAA/2 V1 | 650 | 4 |
| D6 | 76 EA/18 MMA/2 HEA/2 DAA/2 V1 | 780 | 9 |
| D7 | 78 EA/18 MMA/2 DAA/2 V2 | 700 | 6 |
| D8 | 78 nBA/18 MMA/2 DAA/2 V2 | 640 | 5 |
| D9 | 76 EA/18 MMA/2 HEA/2 DAA/2 V2 | 800 | 12 |
| D10 | 78 BA/18 MMA/2 DAA/2 V4 | 460 | 4 |
| D11 | 78 BA/18 MMA/2 DAA/2 VS | 1800 | 18 |
| D12 | 78 HA/18 MMA/2 HEA/2 V2 | 3000 | 28 |
| D13 | 78 EA/18 MMA/2 HEA/2 V4 | 1310 | 16 |
| D14 | 78 EA/20 MMA/2 V1 | 3500 | 35 |
| D15 | 78 EA/20 MMA/2 V2 | 3500 | 35 |

*The polymer dissolved in the solvents and the swelling behavior and the extractables therefore could not be determined.

Abbreviations
EA Ethyl acrylate
nBA n-Butyl acrylate
MMA Methyl methacrylate
HEA Hydroxyethyl acrylate
DAA Diacetoneacrylamide In the case of dispersions D1 to D3, no crosslinking occurs. Self-crosslinking dispersions D4 to D11 contain a crosslinking agent V1 to V5 and a monomer having a keto group. They are readily crosslinkable even at room temperature. The results of dispersions D12 to D15 show that the polymerized oxime ethers can also crosslink with hydroxyl groups (D12, D13) and with themselves (D14, D15).

Examples of wood coatings
Wood coating 1 Initially taken mixture:
80.00 g of sodium laurylsulfate (10 % strength in $H_2O$)
59.90 g of feed 1
30.77 g of feed 2
270.00 g of $H_2O$
Feed 1:
80.00 g of sodium laurylsulfate (10 % strength in H20)
60.00 g of DAAM (20 % strength in $H_2O$)
24.00 g of acrylic acid
12.00 g of divinylbenzene
738.80 g of butyl methacrylate
13.20 g of copolymerizable oxim ether V1
270.00 g of $H_2O$
Feed 2:
4.00 g of sodium persulfate
303.69 g of $H_2O$
Feed 3:
7.36 g of ammonia (25 % strength in $H_2O$)

The initially taken mixture was heated to 85° C. and prepolymerized for 15 minutes. Feed 1 was added in the course of 2 hours and feed 2 in the course of 2.5 hours. After the mixture had been cooled, pH was brought to 7 with feed 3.

Swelling in tetrahydrofuran 580 % by weight
Extractables 5 % by weight
Wood coating 2
Initially taken mixture:
80.00 g of sodium laurylsulfate (10 % strength in $H_2O$)
58.70 g of feed 1
30.77 g of feed 2
294.00 g of $H_2O$
Feed 1:
80.00 g of sodium laurylsulfate (10 % strength in $H_2O$)
20.00 g of AAEM
24.00 g of acrylic acid
12.00 g of divinylbenzene
726.40 g of butyl methacrylate
17.60 g of copolymerized oxim ether V1
294.00 g of $H_2O$
Feed 2:
4.00 g of sodium persulfate
303.69 g of $H_2O$
Feed 3:
7.36 g of ammonia (25 % strength in $H_2O$)

The preparation was carried out similarly to wood coating 1.

Swelling in tetrahydrofuran 490 % by weight
Extractables 84 % by weight

We claim:
1. A copolymer containing from 0.01 to 30% by weight of an oxime ether of the formula

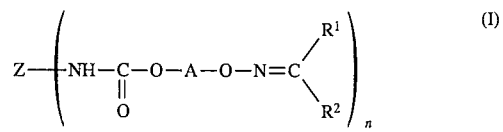

where A is a divalent linking member, $R^1$ and $R^2$ independently of one another are each $C_1$-$C_{10}$-alkyl, $C_1$-$C_{10}$-alkoxy, $C_5$-$C_{10}$-cycloalkyl or $C_5$-$C_{10}$-aryl, each of which may furthermore contain 1–3 nonadjacent nitrogen, oxygen or sulfur atoms as heteroatoms in the carbon chain or in the carbon ring and may be substituted by from one to three $C_1$-$C_4$-alkyl or $C_1$-$C_4$-alkoxy groups, $R^1$ and $R^2$ may be hydrogen or $R^1$ and $R^2$ together form a bridge of 3 to 14 carbon atoms, where some of the carbon atoms may furthermore be part of an aromatic ring, Z is an n-valent organic radical which contains a copolymerizable ethylenically unsaturated group and n is an integer of from 1 to 3.

2. A copolymer as claimed in claim 1, containing a) from 0.01 to 30% by weight of an oxime ether of the formula I b) from 30 to 99.99% by weight of at least one $C_1$-$C_{20}$-alkyl (meth)acrylate, one vinyl ether with carboxylic acids of 1 to 20 carbon atoms, one vinyl aromatic of up to 20 carbon atoms, one ethylenically unsaturated nitrile of 3–6 carbon atoms, one vinyl halide or one nonaromatic hydrocarbon having 4 to 8 carbon atoms and at least 2 conjugated double bonds, c) from 0 to 30% by weight of at least one comonomer having at least one keto or aldehyde group and d) from 0 to 50% by weight of at least one further monomer, the copolymer having a glass transition temperature of from −60 to +140° C.

* * * * *